US00PP34272P2

(12) United States Plant Patent
Hansen

(10) Patent No.: US PP34,272 P2
(45) Date of Patent: May 24, 2022

(54) ***SEDUM* PLANT NAMED 'NIGHT LIGHT'**

(50) Latin Name: ***Sedum* hybrid**
Varietal Denomination: Night Light

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,077

(22) Filed: Feb. 1, 2022

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479
See application file for complete search history.

*Primary Examiner* — Susan McCormick Ewoldt

(57) ABSTRACT

A new and distinct ornamental perennial *Sedum* plant named 'Night Light' is characterized by tight-forming rounded mounds with dark olive-green leaves with greyed-purple glaucous foliage that resists powdery mildew and subsequent scaring. The numerous, wine-colored stems are highly branched and resist lodging in summer heat and rains. Individual flowers of open light-yellow and mature to pink with deep-rose carpels nearly completely covering the top of the plant. The new plant is useful for the landscape in containers, as specimens or en masse.

1 Drawing Sheet

Botanical designation: *Sedum* hybrid.
Cultivar denomination: 'Night Light'.

STATEMENT REGARDING PRIOR DISCLOSURES UNDER 37 CFR 1.77(b)(6)

The claimed plant was first sold by Walters Gardens, Inc. to Prides Corner Farms on Apr. 5, 2021 by Walters Gardens, Inc., who obtained the plant and all information relating thereto, from the inventor. Prior to that, on Feb. 1, 2021, the plant was featured in a non-enabling disclosure of a brief description and photograph on a website operated by Walters Gardens, Inc. and subsequently as a non-enabling disclosure in the "Walters Gardens 2021-2022 Catalog" initially distributed on May 21, 2021. No plants of *Sedum* 'Night Light' have been sold in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of *Sedum* plant, botanically known as *Sedum* and hereinafter referred to by the cultivar name 'Night Light' or the new plant.

The new *Sedum* plant is a selection of a planned breeding program conducted by the inventor, at a wholesale perennial nursery in Zeeland, Mich., USA.

The new *Sedum* plant was selected as a single seedling from an insect-pollination of a proprietary, unreleased, unnamed hybrid known only by the breeder code 12-66-08 at a wholesale perennial nursery in Zeeland, Mich. The seed was collected on Oct. 25, 2013. *Sedum* 'Night Light' was assigned the breeder code number 13-88-11 to keep it separated from among thousands of other seedlings of this and other crosses when it progressed through the initial trial phase in the fall of 2015. The selected single seedling clone was originally selected for its strong, healthy, dense growth, colorful foliage and flowers and intermediate traits between the two parents.

Asexual reproduction of *Sedum* 'Night Light' by division at a wholesale perennial nursery in Zeeland, Mich., USA since October of 2015 and subsequent vegetative shoot tip cuttings has shown that the unique features of this new *Sedum* plant are stable and reproduced true to type in successive generations.

SUMMARY OF THE INVENTION

Plants of *Sedum* 'Night Light' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Night Light' and distinguish it as a new and distinct stonecrop plant unique from all other stonecrop plants known to the inventor:

1. Tight-forming rounded mounds with vertical stems.
2. Center stems remain erect throughout the growing season producing full habit.
3. Foliage is glaucous, dark, olive-green with grey-purple and resists powdery mildew and the subsequent scaring.
4. Numerous, wine-colored stems produce dense flower clusters of light-yellow that mature to pink with deep-rose carpels and nearly completely cover the top of the plant.

In comparison with the parent, the new plant has a larger width and height and retains its upright stems better through the entire growing season. The nearest comparison varieties known to the inventor are: 'Crystal Pink' U.S. Plant Pat. No.

22,094, 'Hot Stuff' U.S. Plant Pat. No. 17,212, 'Night Embers' U.S. Plant Pat. No. 29,211, 'Coraljade' U.S. Plant Pat. No. 33,958, 'Black Jack' U.S. Plant Pat. No. 16,736, 'Back in Black' U.S. Plant Pat. No. 33,632 and 'TNSEDPP' U.S. Plant Patent Application by another applicant.

'Crystal Pink' has creamy-green buds that open to light-pink and the stems, and the leaves are green. 'Hot Stuff' creamy buds that open to medium-pink and mature with reddish-purple carpels, and the stems and leaves are green. 'Night Embers' has foliage that is less glaucous and more glossy and darker burgundy, the habit is more upright and less mounded, and the flowers are light mauve-pink. 'Coraljade' has foliage that is larger and not as deep burgundy tinted and the flowers are more coral-colored and age to a more bronze coloration. 'Black Jack' is more upright, with darker burgundy foliage that is more susceptible to powdery mildew, and the flowers are deeper pink. 'Back in Black' is taller and more upright with darker foliage and the carpels are more crimson. 'TNSEDPP' (also sold under the cultivar name 'Peach Pearls') has a more upright habit and less mounded, with less flower coverage in peak bloom, and the flowers are a deeper burnt yellow and do not have a pink tepal phase.

The parent, 12-66-08, has a taller and less full habit, darker burgundy foliage, it tended to lodge later late in the season, and the flowers were deeper pink.

BRIEF DESCRIPTION OF THE PHOTOGRAPHS

The photograph of the new plant demonstrates the unique traits and the overall appearance of *Sedum* 'Night Light'. The colors are as accurate as reasonably possible with color reproductions of this type. Variations in ambient light spectrum, source and direction may cause the appearance of minor variation in color. The plants used in the photograph were four-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
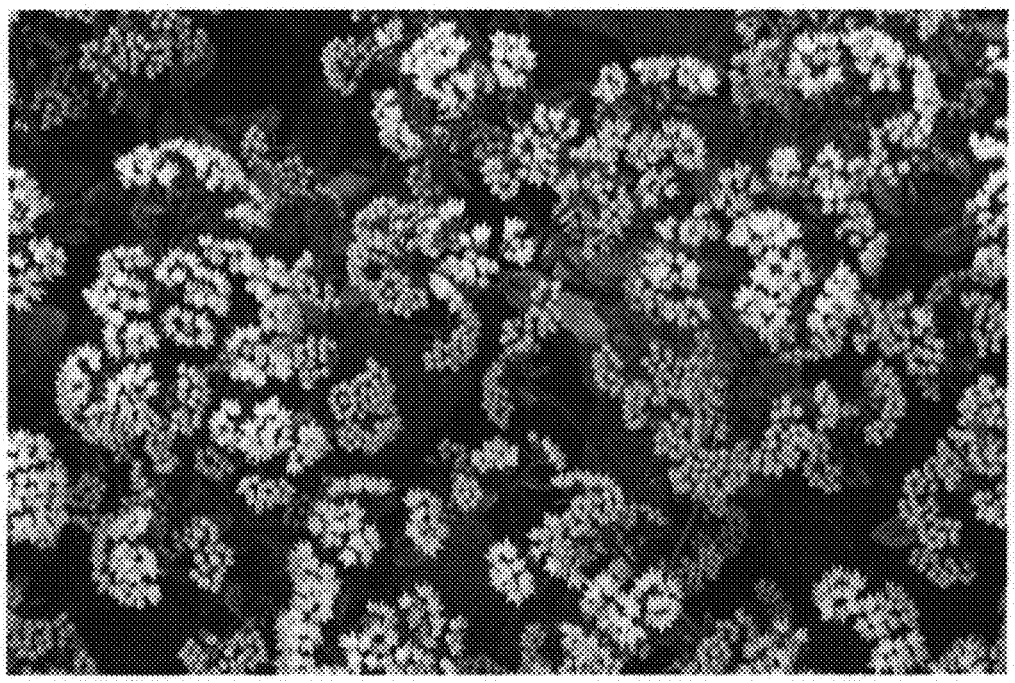
FIG. 1 shows a close-up of the flowers and buds of the new plant in mid-summer.
Figure 2:
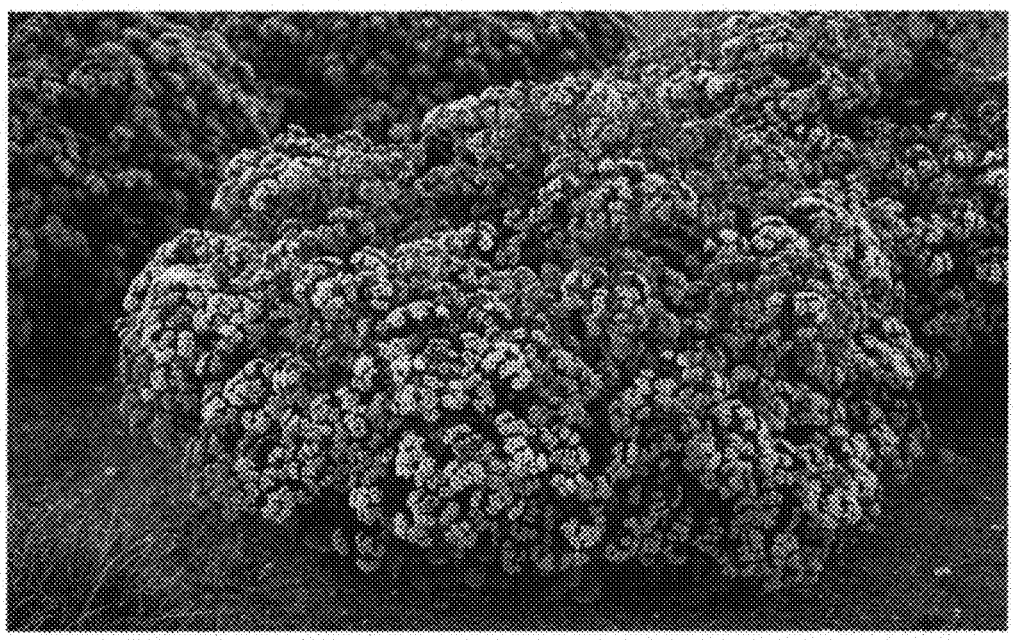
FIG. 2 shows the habit of the new plant with foliage in early stages of flowering.

The following is a detailed description of four-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Night Light';

Parentage: The female parent is an unnamed proprietary hybrid known only by the breeder code 12-66-08; the male parent is unnamed, but may have been any one of a number of other siblings in the isolation block hybridizing area;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color;

Plant habit: Winter-hardy herbaceous perennial; upright mound; stiff upright stems; dense and full, not opening in center later in the season; flower heads freely branching;

Growth rate: Moderately vigorous;

Plant size: About 49.0 cm tall and 74.0 cm wide in full flower;

Stems: Terete; glaucous; glabrous; diameter at base to about 16.0 mm, average about 12.0 mm; heavily branched in distal portion; about 15.0 cm long from base to initial branches; about 9 stems per plant and 10 branches per stem;

Stem color: Proximally or in shade nearest RHS 147C, distally nearest RHS N186C, with full glaucous coating nearest RHS N187B;

Lateral branches: To about 10 per stem; glaucous; glabrous; terete; primary branches to about 25.0 cm long and about 6.0 mm diameter at base;

Lateral branch color: Nearest RHS N186C;

Foliage: Ovate; spirally arranged; simple; smooth; sarcous; glabrous and glaucous on both surfaces; sessile; thick; apex bluntly acute to rounded; base attenuate; margin irregularly and shallowly dentate, 8 to 14 teeth; teeth about 1.0 mm, to 1.5 mm apart; decreasing in size distally; attitude outward; about 34 per stem;

Foliage size: To about 8.5 cm long, 5.4 cm across and 4.0 mm thick at midrib; average about 5.2 cm long, 3.1 cm across and 2.6 mm thick; decreasing distally;

Foliage color: Adaxial young between RHS N187C and RHS 189B, abaxial young nearest RHS 189B; mature adaxial nearest RHS N187A and abaxial between RHS 191A and RHS N138C variably blushed with nearest RHS N187A;

Petiole: Leaves sessile;

Venation: Palmate, barely distinguishable; slightly raised abaxial;

Vein color: Adaxial midrib nearest RHS N187A and abaxial midrib between RHS 191B and RHS N138C; secondary veins not obvious;

Flower: Stellate, actinomophic; perfect; complete; pentamerous; persistent; attitude upright to outwardly in terminal compound cymes; size about 6.0 mm across at petal apices and 5.0 mm tall;

Flower number: About 150 to 200 per branch and 1,000 to 1,700 flowers per stem and 8,000 to 15,000 per plant;

Fragrance: None detected;

Flowering season: Beginning mid-summer in Zeeland, Mich. for about three weeks;

Longevity: Flower cymes remain effective for about three weeks on the plant and one week as cut flowers; individual flowers and calyces persistent and effective for about two weeks;

Flower buds about one day prior to opening: Ellipsoidal; apex acute; base truncate; about 4.0 mm long and about 3.0 mm diameter near middle;

Flower bud color: Exposed petals nearest RHS 11D with distal midrib nearest RHS 145C; calyx nearest RHS N138B;

Inflorescence: To about 22.0 cm tall from first branch and about 36.0 cm across; up to about 1,500 flowers per inflorescence;

Petals: Typically five; broadly-lanceolate; acute apex; base truncate and fused; margin entire; glabrous abaxial and adaxial; about 5.0 mm long and about 2.3 mm across at middle;

Petal color: Upon opening adaxial nearest RHS NN155B proximally and RHS 145D distally, upon opening abaxial nearest RHS NN155B proximally and RHS 145B distally; adaxial maturing to between RHS 158A and RHS 158B distally and proximally nearest RHS 158D; abaxial maturing to between RHS 158A and RHS 158B distally and proximally nearest RHS 158D;

Calyx: With five sepals; campanulate to stellate; about 4.0 mm across and 3.0 mm deep;

Sepals: Linear to lanceolate; narrowly acute apex; fused base; entire margin; glabrous and slightly glaucous both abaxial; adpressed to petals, about 2.0 mm long beyond fusion and about 1.5 mm across at fusion;

Sepal color: Nearest RHS N138B;

Peduncles: Terete; glaucous, glabrous, becoming lustrous; stiff and flexible; freely branching; mostly upwardly to slightly outwardly; with branches to about 45° from perpendicular; to about 20.0 cm long and 5.0 mm diameter;

Peduncle color: Nearest RHS 146C, and with exposure to high ultraviolet light nearest RHS N186C where bloom washed or rubbed away and nearest RHS N186B with bloom remaining;

Pedicels: Cylindrical; glabrous; glaucous, becoming lustrous; strong and stiff, yet flexible; to about 4.0 mm long and 0.7 mm diameter; average about 3.0 mm long and 0.5 mm diameter;

Pedicel color: Blend between RHS N138B and with a slight blush of nearest RHS N186C;

Androecium: Typically five stamens, rarely with five additional undeveloped;

*Filaments*.—Cylindrical; upwardly; free, not adnate inner corolla; about 2.0 mm long and about 0.3 mm diameter; color translucent to nearest RHS NN155D.

*Anthers*.—Basifixed; longitudinal; ellipsoidal; about 0.7 mm long and 0.6 mm across; color nearest RHS 10B.

*Pollen*.—Moderate in quantity; color nearest RHS 8D.

Gynoecium: Typically five; cylindrical, conic in distal one third; to about 5.0 mm long and 1.5 mm diameter;

*Style*.—Terete conical; tapering distally with base truncate; about 1.0 mm long and 0.5 mm diameter at point of attachment to ovary; glabrous; lustrous; color initially upon opening nearest RHS 145B, progressing to nearest RHS 59B at maturity.

*Stigma*.—Minute, acute; about 0.2 mm diameter and 0.2 mm long; color initially upon opening nearest RHS 158D, progressing to nearest RHS 59B at maturity.

*Ovary*.—Conical; acutely tapering at apex to style; base truncate; lustrous; about 4.0 mm long and 1.5 mm diameter; color initially upon opening nearest RHS 160C, progressing to nearest RHS 160D proximally and nearest RHS 59B distally at maturity, with petals marcescent nearest RHS 46A distally and nearest RHS 160D proximally.

Fruit: Ventrally dehiscent follicle; about 3.5 mm long and 3.2 mm across; color at maturity nearest RHS 177A;

Seed: Sparse; fine; lanceolate; about 1.0 mm long and less than 0.2 mm across; color between RHS 165A and RHS 165B;

Growing conditions: Plants of the new *Sedum* 'Night Light' is xeromorphic and grow best with good drainage, full sun and moderate to low fertility. 'Night Light' tolerates heavy rains and wind and is not prone to develop an open center later in the season as many other *Sedum* cultivars do that are known to the inventor.

Hardiness: The new plant is cold hardy from USDA zones 3 to 9 and has tolerated temperatures of at least 35 degrees C.

Disease and pest resistance: Other pest and disease resistance and tolerance outside that normal for *Sedum* is not known.

It is claimed:

1. A new and distinct perennial *Sedum* plant named 'Night Light' as herein described and illustrated.

* * * * *